US00PP35449P2

(12) United States Plant Patent
von Tubeuf

(10) Patent No.: US PP35,449 P2
(45) Date of Patent: Oct. 31, 2023

(54) POINSETTIA PLANT NAMED 'NPCW22387'

(50) Latin Name: *Euphorbia pulcherrima*
Varietal Denomination: NPCW22387

(71) Applicant: KLEMM + SOHN GMBH & CO. KG, Stuttgart (DE)

(72) Inventor: Guido von Tubeuf, Stuttgart (DE)

(73) Assignee: KLEMM+ SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/084,781

(22) Filed: Dec. 20, 2022

(51) Int. Cl.
*A01H 5/12* (2018.01)
*A01H 6/38* (2018.01)

(52) U.S. Cl.
USPC ..... Plt./304

(58) Field of Classification Search
USPC ..... Plt./304
CPC ... A01H 5/02; A01H 5/12; A01H 5/00; A01H 6/38; A01H 6/385
See application file for complete search history.

(56) References Cited

U.S. PATENT DOCUMENTS

PP29,224 P2 * 4/2018 Nebelmeir ..... A01H 6/385 Plt./304

OTHER PUBLICATIONS

Adam PennState Extension Poinsettiss—What's New with this Old Plant 2021, retrieved on Mar. 1, 2023 at https://extension.psu.edu/poinsettias-whats-new-with-this-old-plant, 2 pp. (Year: 2021).*

Floral Daily New home poinsettia & kalanchoe catalog 2022, retrieved on Mar. 1, 2023 at https://www.floraldaily.com/article/9382554/new-home-poinsettia-kalanchoe-catalog-2022/, 3 pp. (Year: 2022).*

Selecta One Home Poinsettia Kalanchoe 2023 retrieved on Mar. 1, 2023 at https://docs.gestionsweb.cat/2389/cata-logo-poinsettia-2023-compressed-1995064.pdf, cover page, 1 introductory page, 1 and 18-19. (Year: 2023).*

Selecta One Poinsettias 2022 retrieved on Mar. 1, 2023 at https://www.ballseed.com/PDF/Catalogs/Poinsettia2022_Catalog_SEL_211810828.pdf, cover page, 1 introductory page, pp. 1-2, 32 and 48 (Year: 2022).*

CPVO Register S2/S3 version 4.9.9, retrieved on Jun. 22, 2023 at https://online.plantvarieties.eu/publicConsultationDetails?registerId=20230599&denomination=npcw22387, 2 pp. (Year: 2023).*

* cited by examiner

*Primary Examiner* — June Hwu
(74) *Attorney, Agent, or Firm* — Weatherly IP Solutions, LLC; James M. Weatherly

(57) ABSTRACT

A new poinsettia plant particularly distinguished by having a low vigor, wider growth habit, white bract color, and more elongated bract shape, is disclosed.

1 Drawing Sheet

Genus and species: *Euphorbia pulcherrima.*
Variety denomination: 'NPCW22387'.

BACKGROUND OF THE NEW PLANT

The present invention comprises a new and distinct variety of poinsettia, botanically known as *Euphorbia pulcherrima* and hereinafter referred to by the variety name 'NPCW22387'. 'NPCW22387' is a selection from a controlled crossing conducted in December 2017 in Nairobi, Kenya between the proprietary female *Euphorbia* line 'NPCW12197' (U.S. Plant Pat. No. 24,539) and the male *Euphorbia* line 'LAZZPO1319' (U.S. Plant Pat. No. 29,243). A plant line was selected in October 2018 in Stuttgart, Germany and named 'NPCW22387'. In May 2019, 'NPCW22387' was first vegetatively propagated by apical cuttings. 'NPCW22387' was found to reproduce true to type in successive generations of asexual propagation via apical cuttings in Stuttgart, Germany.

SUMMARY

The following are the most outstanding and distinguishing characteristics of this new variety when grown under normal horticultural practices in Stuttgart, Germany.

1. Low vigor;
2. Wider growth habit;
3. White bract color; and
4. Elongated bract shape.

DESCRIPTION OF THE PHOTOGRAPH

This new poinsettia plant is illustrated by the accompanying photograph which shows an overall view of the plant. The photograph is of a plant approximately fourteen-weeks-old, grown indoors Stuttgart, Germany in December 2020. The colors shown are as true as can be reasonably obtained by conventional photographic procedures.

DESCRIPTION OF THE NEW VARIETY

The following detailed descriptions set forth the distinctive characteristics of 'NPCW22387'. The data which define these characteristics were collected from asexual reproductions carried out in Stuttgart, Germany. Data was collected on thirteen week old plants grown indoors in Stuttgart, Germany in December 2022 under greenhouse conditions. Color references are to The R.H.S. Colour Chart of The Royal Horticultural Society of London (R.H.S.), $5^{th}$ edition (2007).

Classification:
*Family*.—Euphorbiaceae.
*Species*.—*Euphorbia pulcherrima*.
*Common name*.—Poinsettia.
*Variety*.—'NPCW22387'.

Parentage:
*Male*.—*Euphorbia* line 'LAZZPO1319' (U.S. Plant Pat. No. 29,243).
*Female*.—*Euphorbia* line 'NPCW12197' (U.S. Plant Pat. No. 24,539).

Plant:
*Form*.—Triangular.
*Growth habit*.—Broad upright.
*Height*.—22.0 cm.
*Width*.—35.0 cm.
*Average number of inflorescences per plant*.—5.
*Keeping quality*.—Very good.
*Time to produce a cutting*.—5 to 6 weeks.
*Flowering response time*.—Approximately 57 days.

Propagation:
*Type cuttings*.—Apical cuttings.
*Rooting habit and root color*.—Freely branching and RHS NN155C (White).

Lateral branches:
*Color*.—RHS 143C.
*Length*.—24.0 cm to 25.0 cm.
*Internode length*.—1.5 cm to 3.0 cm.
*Diameter*.—0.4 cm to 0.5 cm.
*Branching habit*.—Freely branching.
*Number of lateral branches per plant*.—5.
*Texture*.—Smooth.
*Strength*.—Sturdy.
*Anthocyanin*.—Absent.

Leaves:
*Quantity*.—5 to 6 per lateral branch.
*Arrangement*.—Alternate.
*Number of lobes on the leaf blade*.—1 to 5.
*Lobation depth*.—Some shallow lobes and 1 to 2 deeper lobes.
*Depth of the deepest sinus of the leaf blade*.—0.8 cm.
*Shape*.—Obtuse.
*Apex*.—Acuminate.
*Base*.—Rounded.
*Margin*.—Entire, slightly serrated.
*Length*.—8.0 cm to 11.0 cm.
*Width*.—4.0 cm to 7.0 cm.
*Texture*.—Upper surface: Smooth. Lower surface: Slightly pubescent.
*Vein color*.—Upper surface: The veins are transparent but show the yellow-green color of the leaf. Lower surface: RHS 145C.
*Variegation*.—Absent.
*Venation pattern*.—Reticulate.
*Color*.—Mature foliage: Upper surface: Closest to RHS 139A. Lower surface: RHS N138A. Immature foliage: Upper surface: RHS 141B. Lower surface: RHS N137D.
*Leaf petiole*.—Length: 3.0 cm to 5.0 cm. Diameter: 0.2 cm. Color: Upper (part) surface: RHS 143C. Lower (part) surface: RHS 145B. Texture: Smooth. Strength: Medium. Transitional leaves: Few. Transitional leaves lobing intensity: Weak. Color: Upper surface: Closest to RHS 139A with variable degrees of white coloration. Lower surface: RHS N138A with variable degrees of white coloration. Anthocyanin: Absent.

Inflorescence:
*Type and habit*.—Cluster of cyathia surrounded by bracts.
*Quantity per lateral branch*.—1.
*Position relative to foliar plane*.—Above.
*Lastingness of inflorescence on the plant*.—4 to 5 weeks.
*Natural flowering season*.—End of November.
*Diameter*.—18.0 cm to 23.0 cm.
*Height*.—1.0 cm to 1.5 cm.
*Fragrance*.—Absent.

Bracts:
*Number of bracts per inflorescence*.—7 to 9.
*Shape*.—Obtuse.
*Apex*.—Acuminate.
*Base*.—Rounded.
*Margin*.—Entire and slightly lobed.
*Size*.—Length: 7.0 cm to 12.0 cm. Width: 3.0 cm to 6.0 cm.
*Texture* (*both upper and lower surfaces*).—Smooth.
*Folding along the main vein*.—Absent.
*Twisting*.—Absent.
*Rugosity between the veins*.—Medium.
*Venation pattern*.—Reticulate.
*Vein color*.—Upper surface: RHS 143B. Lower surface: RHS 144D.
*Bract color*.—Upper surface: RHS 157D. Lower surface: RHS 1D.
*Bract petiole*.—Length: 0.5 cm to 1.5 cm. Diameter: 0.2 cm. Color: Upper (part) surface: RHS 144B. Lower (part) surface: RHS 144B. Texture: Smooth. Strength: Medium.

Cyme:
*Diameter*.—2.0 cm to 2.5 cm.
*Cyathia number*.—7.0 cm to 8.0 cm per inflorescence.
*Deformation of glands of the cyathium*.—Absent.
*Timing of opening of cyathia*.—Opens end of November; first pollen appears in parallel to opening of the nectar cups, stigmas appear 2 to 3 weeks later.
*Cyathium*.—Shape: Ovate. Texture: Smooth. Diameter: 0.3 cm to 0.4 cm. Length: 0.5 cm to 1.0 cm. Color: RHS 143B.
*Peduncle*.—Color: RHS 142B. Length: 0.2 cm. Diameter: 0.1 cm. Texture: Smooth. Strength: Sturdy.
*Nectar cups*.—Number: 1 per cyathium. Diameter: 0.1 cm. Length: 0.3 cm. Color: RHS 144D. Shape: Lip shaped. Texture: Smooth.

Reproductive organs: Not observed.

Fruit and seed set: Not observed.

Disease and insect resistance: No particular disease or insect resistance observed.

COMPARISON WITH PARENTAL LINE AND KNOWN VARIETY

'NPCW22387' is distinguished from its mutation parent as described in Table 1:

TABLE 1

| Comparison with Parental Lines | | | |
|---|---|---|---|
| Trait or characteristic | Instant variety 'NPCW22387' | Female parent 'NPCW12197' | Male Parent 'LAZZPO1319' |
| Vigour | Low | Medium | High |
| Growth habit | Wider | Medium | More upright |
| Bract color | White | Red | Very light yellow appearing close to white in color |

COMPARISON WITH SIMILAR VARIETY

'NPCW22387' is most similar to the commercial poinsettia plant named 'LAZZPO1315' (U.S. Plant Pat. No. 29,224). Differences between the two varieties are described in Table 2:

TABLE 2

| Trait | Variety 'NPCW22387' | Commercial line 'LAZZPO1315' |
|---|---|---|
| Vigor | Low | Medium |
| Growth habit | Wider | More upright |
| Bract shape | More elongated | Broader |

I claim:

1. A new and distinct cultivar of Poinsettia Plant Named 'NPCW22387' as described and illustrated herein.

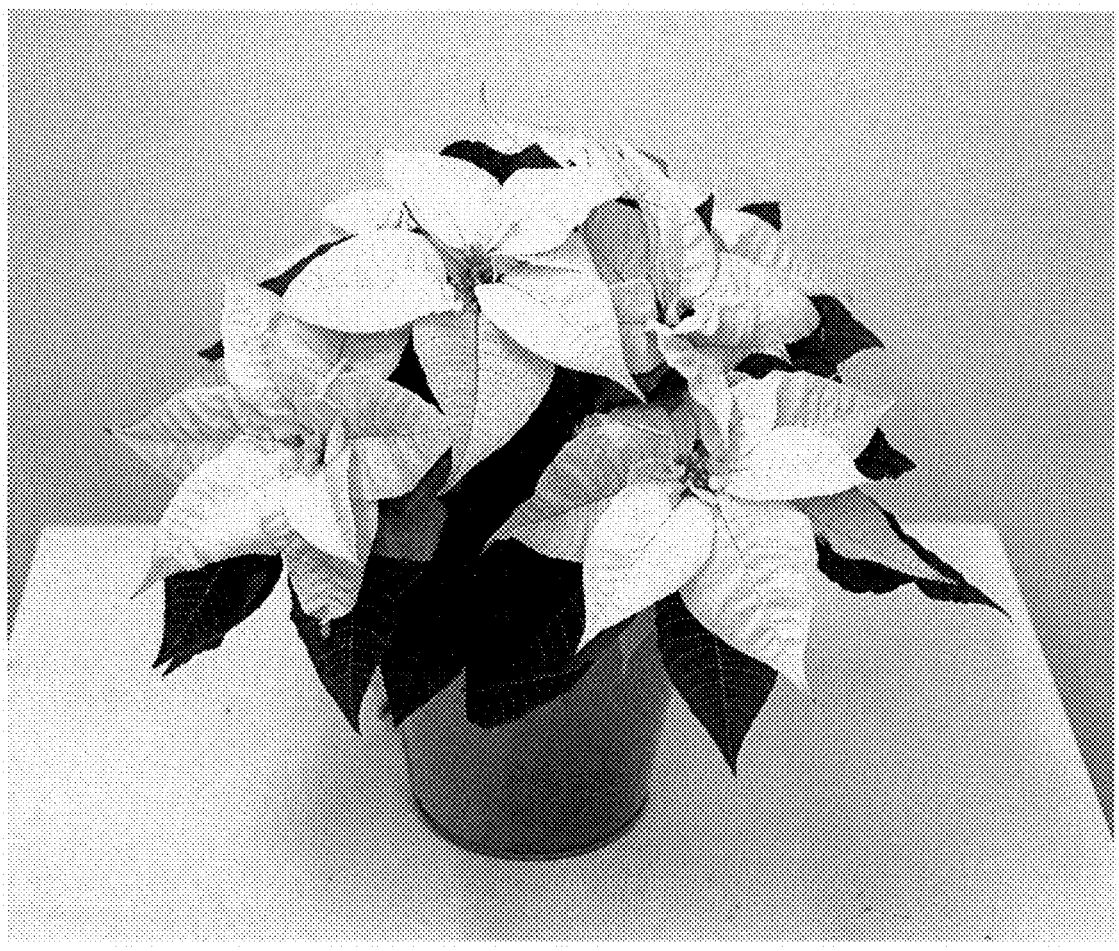

* * * * *